United States Patent [19]
White

[11] 3,933,864
[45] Jan. 20, 1976

[54] PROCESS FOR PREPARING GLYCIDONITRILES

[75] Inventor: David R. White, Kalamazoo, Mich.

[73] Assignee: The Upjohn Company, Kalamazoo, Mich.

[22] Filed: Dec. 10, 1974

[21] Appl. No.: 531,431

[52] U.S. Cl. .............................................. 260/348 R
[51] Int. Cl.² .................................... C07D 303/46
[58] Field of Search ............................... 260/348 R Primary Examiner—Norma S. Milestone
Attorney, Agent, or Firm—John T. Reynolds

[57] ABSTRACT

Process for preparing glycidonitriles in which a ketone or aldehyde is reacted with chloroacetonitrile under substantially anhydrous conditions using inorganic alkali metal bases in a solvent medium containing at least about 3 percent liquid volume of a dipolar, aprotic liquid such as dimethylformamide, any balance of solvent being a nonpolar organic liquid.

8 Claims, No Drawings

3,933,864

PROCESS FOR PREPARING GLYCIDONITRILES

INTRODUCTION

This invention relates to processes for preparing glycidonitriles. More particularly, this invention provides an improved process for preparing glycidonitrile compounds in high yields more economically than by previously known processes.

BACKGROUND OF THE INVENTION

Recently, processes have been developed for the synthesis of useful carboxylic acids from glycidonitriles. See, Argentina Pat. Nos. 198,097 and 198,595 for examples.

The preparation of glycidonitriles from aromatic ketones is known. See J. Gen. Chem., U.S.S.R. 27, pp. 1188–1189 (1957) and J. Am. Chem. Soc., 82, 4315 (1960). However, published yields of glycidonitriles have not exceeded about 80 percent, and those processes have involved the use of expensive bases such as potassium tibutoxide.

In J. Org. Chem., Vol. 37, No. 16, (1972), page 2573, James Cason et al. disclose the cyanoethylation of 2-octanone with solid potassium hydroxide in dimethoxyethane, in which system the basicity of the potassium hydroxide is enhanced substantially. However, none of the products there produced were or relate to the formation of glycidonitriles.

Later glycidonitrile making processes have been developed by the inventor herein which processes give almost quantitative yields of the glycidonitrile when sodium ti-amylate is used as the base. However, that organic base is also expensive. Those in the chemical process development art are seeking more economical processes for making glycidonitriles which are of importance now as intermediates to make a variety of known and useful carboxylic acids and derivatives thereof. See Tetrahedron Letters (1972) page 7395.

OBJECTS OF THE INVENTION

It is an object of this invention to provide an improved process for preparing glycidonitrile compounds.

It is a further object of this invention to provide process for making glycidonitriles under solvent conditions such that the basicity of economical, readily available inorganic bases can be enhanced substantially so as to allow high yields (over 90 percent) of glycidonitriles under more economical conditions.

Other objects, advantages, and aspects of this invention will become apparent from reading the remainder of the specification and claims which follow.

SUMMARY OF THE INVENTION

Briefly, by this invention I have discovered that high yields (over 90 percent) of glycidonitrile product can be obtained and the isolation of the glycidonitrile from the reaction mixture can be made easier by a process involving the use of the economical inorganic bases in an organic liquid system. This invention comprises reacting a ketone or aldehyde, with chloroacetonitrile in the presence of a solid form alkali metal or alkaline earth metal hydroxide under substantially anhydrous conditions in a solvent mixture containing at least about 3 percent by liquid volume based upon the volume of the total reaction mixture, of an dipolar, aprotic organic compound which is liquid at the reaction temperature, any remaining solvent medium being a nonpolar, organic liquid for a time sufficient to form glycidonitrile product.

DETAILED DESCRIPTION OF THE INVENTION

More specifically, this invention provides an improved process for preparing a glycidonitrile of the formula

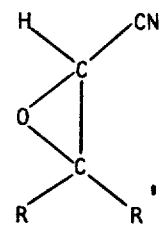

wherein R, when taken separately, is hydrogen or an aliphatic, alicyclic, aromatic or heterocyclic group, R', when taken separately, represents an aliphatic, alicyclic, aromatic or heterocyclic group, and R and R', when taken together and connected, represent an alicyclic or heterocyclic group.

Included among the aliphatic, alicyclic and aromatic groups which R and R' can each represent when taken separately are, for example, alkyl (including saturated and unsaturated, straight and branched chain alkyl and cycloalkyl) and aryl (including alkaryl and aralkyl) radicals, such as methyl, ethyl, propyl, isopropyl, n-butyl, sec. butyl, tert. butyl, amyl, hexyl, heptyl, octyl, decyl, dodecyl, octadecyl, vinyl, allyl, methallyl, butenyl, pentenyl, hexenyl, heptenyl, octenyl, ethynyl, propynyl, butynyl, pentynyl, hexynyl, heptynyl, octynyl and isomeric forms thereof, cyclobutyl, cyclopentyl, cyclohexyl, 1-cyclohexenyl, methylcyclohexyl, cycloheptyl, cyclooctyl, cyclooctyl, cyclodecyl, cycloundecyl, cyclododecyl, cyclopentadecyl, phenyl, tolyl, xylyl, benzyl, phenethyl, phenylpropyl, benzhydryl, naphthylmethyl, o-carboxylbenzyl, and the like, as well as fused and bridged ring structures, such indanyl, indenyl, naphthyl, acenaphtyl, phenanthryl, cyclopentanopolyhydrophenantheyl, adamantanyl, bicyclo[3:1:1]heptyl, bicyclo[2:2:2]octyl and the like; all of which can either be unsubstituted or substituted with one or more non-interfering substituents, such as hydroxyl derivatives, for example, alkoxy such as methoxy, ethoxy, propoxy, butoxy, and the like; acyloxy, such as acetoxy, propionoxy, butyroxy and the like; nitro groups; amino groups; alkylamino groups, such as methylamine, ethylamino, dimethylamino and the like; halogens, such as fluorine, chlorine, or bromine; carbonyl derivatives such as enol ethers and ketals; and the like.

Included among the heterocyclic groups which R and R' can represent are substituted and unsubstituted azabicycloalkane groups such as azabicyclo[3:2:2]octyl and azabicyclo[3:2:1]nonyl and the like, furfuryl groups, tetrahydrofurfuryl groups, piperidyl groups, pyrrolidyl groups, pyridyl groups, thiophene groups, alkaloid nuclei groupings containing for example indole, dihydroindole, quinolidine, quinthio groups and the like.

Included among the alicyclic and heterocyclic groups in which R and R' when taken together and connected can represent, are cyclopropyl, cyclobutyl, cyclohexyl, dicyclohexyl, cyclodecyl, cyclododecyl, cyclopentadecyl, and the like, piperidyl, pyrrolidyl, and the like; fused ring systems such as cyclopentanopolyhydrophenanthranyl, indanyl, indenyl, and the like, bridged ring systems such as adamantyl, bicyclo[2:2:1]heptyl, bicyclo[2:2:2]octyl, bicyclo[3:2:2]nonyl, azabicycloalkyls, and the like, all of which can be substituted by non-interfering substituents such as those hereinbefore named.

These glycidonitrile compounds are prepared by reacting a ketone or aldehyde of the formula

where R and R' are as defined above, with chloroacetonitrile, in the presence of a solid form of alkali metal hydroxide under substantially anhydrous conditions in a liquid mixture containing at least 3 percent of the total liquid volume of a dipolar, aprotic liquid solvent. In addition to the dipolar, aprotic liquid solvent the reaction liquid contains the ketone or aldehyde, the chloroacetonitrile, any remainder of the solvent mixture being a nonpolar, organic liquid. Examples of dipolar, aprotic compound which can be used include the bis($C_1$ to $C_4$-alkyl)carboxylic $C_1$ to $C_3$-acylamides such as dimethylformamide, diethylformamide, dipropylformamide, dibutylformamide, dimethylacetamide, diethylacetamide, dimethylpropionamide, and the like, the bis($C_1$ to $C_4$-alkyl) sulfoxides such as dimethylsulfoxide, diethylsulfoxide, dipropylsulfoxide, dibutylsulfoxide and the like, and hexa($C_1$ to $C_2$-alkyl)pentavalent phosphoric amides such as hexamethyl-orthophosphoramide, tetramethyl (phenyl)-phosphonamide, and the like, which are liquids or become liquids at the reaction temperatures. For reasons of ready availability and economy of operation dimethylformamide, diethylformamide, dimethylsulfoxide, or hexamethylorthophosphoramide are preferred for use as the dipolar, aprotic solvent in the mixture.

For practical reasons of speed of reaction, the reaction mixture preferably contains at least about 6 percent by liquid volume of the dimethylformamide, dimethylacetamide, or dimethylsulfoxide. For ease of separating the glycidonitrile solution from the water soluble components of the reaction mixture I prefer to use a combination of the dimethylformamide, dimethylacetamide or dimethylsulfoxide and the non-polar organic liquid diluent as a medium for the glycidonitrile formation reaction. The reaction may be conducted at any temperature in which can be maintained in the liquid condition. However, for most combinations of reactants and solvents, temperatures ranging from about 0° to about 50° C. are adequate and preferred to accomplish the glycidonitrile product formation in reasonable time periods, say, within about 10 hours.

The dipolar, aprotic substance can be used as the only solvent medium for the reactants. However, it is preferred to dilute the dipolar, aprotic substance with a nonpolar organic liquid which preferably constitutes the major liquid volume constituent in the mixture. The nonpolar, organic liquid will generally be selected from the economical, recoverable aromatic and saturated aliphatic hydrocarbon, halogenated solvents and ethers such as benzene, toluene, xylene, chlorobenzenes, hexane, heptane, tetrahydrofuran, diglyme and commercially available mixtures of pentane, bp. 28°–30° C., hexane, bp. 60°–68° C., heptane, bp. 90°–100° C., mixed heptanes, bp. 77°–115° C., mixed octanes, bp. 100°–140° C., petroleum ether mixtures, bp. 30°–60° C., and bp 40°–75° C., mixtures of hexanes and heptanes bp. 69°–96° C., octane mixtures, bp. 95°–127° C. and the like, which are available under various brand names such as Skellysolve with letter designations such as A to L following the trademark. See Merck Index, Eighth Edition, page 951. Toluene is presently preferred for reasons of economics, success with its use, and safety for the personnel involved.

The dipolar, aprotic solvent can be added to the reaction vessel prior to or substantially simultaneously with any non-polar organic liquid and the reactants to form the reaction mixture. Alternatively a solvent mixture consisting essentially of the major proportion by volume of the non-polar organic liquid and at least 3 percent, preferably at least 6 percent by volume of the dipolar, aprotic solvent can be prepared prior to mixing therein the ketone or aldehyde, the chloroacetonitrile and the solid alkali metal hydroxide reactants. Other dialkylcarboxylic acyl amides or dialkyl sulfoxides could be used in mixtures with dimethylformamide, dimethylacetamide or dimethylsulfoxide. However, these are economical and perform efficiently in this process. The solvents listed here and the mixtures herein are intended within reason to provide a substantially anhydrous reaction medium. However, it is to be understood that the reaction will proceed in the presence of minor incidental amounts of water which may be introduced to the reaction vessel with selected solvents or reactants with only minor effect on the yields of the glycidonitrile product.

The term "alkali metal hydroxides" as used herein is intended to include the use of commercially available alkali metal hydroxides which contain up to about 5 percent by weight of alkali metal carbonate, or mixtures of alkali metal hydroxide and alkali metal carbonate, wherein the alkali metal carbonate content of the mixture should be at most about 5 percent of weight.

Alkali metal hydroxides which can be used are the solid forms of the compounds in granular, flake, pellet or powder form. Sodium hydroxide and potassium hydroxide are the preferred alkali metal hydroxides. Alkaline earth metal hydroxides such as calcium hydroxide and magnesium hydroxides can also be used but are not preferred. In these mixtures the alkali metal hydroxide is not soluble to any appreciable extent and remains suspended therein as the mixture is stirred during the reaction time. Nevertheless, I have found that these hydroxide compounds in these solvent systems provide sufficient basicity to promote the reaction of the ketone or aldehyde and the chloroacetonitrile to form the desired glycidonitrile product while minimizing if not eliminating conceivable side reactions to produce yield lowering by-products.

The alkali metal or alkaline earth metal hydroxide is generally provided to the reaction mixture in an amount which is at least stoichiometrically equivalent to the quantity of the most expensive reactant which is usually the ketone or aldehyde reactant. From 1 to 3 molar equivalents of the base is generally sufficient for most reaction mixture combinations.

The dipolar, aprotic liquid components, that is the dimethylformamide, dimethylacetamide or dimethylsulfoxide or preferably the mixture thereof with the non-polar organic liquid solvent is used in an amount to at least partially dissolve the ketone or aldehyde and the chloroacetonitrile reactants, to uniformly suspend the base in the mixture and to evenly absorb or distribute any heat of reaction which may occur. Generally, on a 0.1 mole scale reaction of the ketone or aldehyde with the chloroacetonitrile a 2 to 6 ml. volume of dimethylformamide, dimethylacetamide or dimethylsulfoxide or mixture thereof with the non-polar organic liquid is sufficient to effect substantially complete reaction to the glycidonitrile product. However, more concentrated or more dilute reaction mixtures can be used.

Chloroacetonitrile is the preferred reagent to use in this process for making glycidonitriles, because it is the most readily available and economical. However, other haloacetonitriles such as bromoacetonitrile and iodoacetanitrile could also be used, but in the use of those haloacetonitriles, the preferred temperature and solvent proportions would vary somewhat. The chloroacetonitrile is preferably added gradually to a mixture of the other components to maintain better control of the reaction, although the chloroacetonitrile could be added all at once. I have used chloroacetonitrile addition times ranging from 2 to 60 minutes to obtain substantially quantitative yields of glycidonitrile in these reaction mixtures. To insure complete reaction of the more expensive ketone or aldehyde, chloroacetaldehyde is preferably added until analysis samples of the reaction mixture, e.g., by gas liquid chromatography, indicate that no more ketone or aldehyde is present.

When the reaction is completed, the reaction mixture can be filtered or decanted to separate filterable solids such as alkali metal hydroxide and alkali metal halide, and then diluted with water and non-polar solvent, if necessary, to effect a separation of phases. The bulk of the glycidonitrile product remains in the organic phase. The water phase may be washed with non-polar organic liquid to recover traces of glycidonitrile product therefrom. The organic phase can be washed one or more times with water to remove traces of the dipolar, aprotic solvent and any other substances which are soluble therein. Thereafter, organic liquid phase containing the glycidonitrile product can be treated by conventional methods to decolorize, dry and recover the glycidonitrile product. Such procedures can include vacuum distillation, solvent extraction in the case of products which are liquids at ambient temperatures, and crystallization, re-dissolution and re-crystallization procedures when the glycidonitrile is a solid. However, when the glycidonitrile is to be used to prepare a carboxylic acid or derivative, the glycidonitrile may be maintained in the non-polar organic liquid medium until it is needed.

The invention is further exemplified by the following detailed examples, but these examples are not intended to limit the scope of the invention.

EXAMPLE 1

A 250 ml. 3-necked flask is fitted with a mechanical stirrer, thermometer, 50 ml. addition funnel and nitrogen inlet. The flask is charged with 12.3 g. of technical grade solid (flake or pellet) sodium hydroxide, 4 ml. of dimethylformamide and 17.60 g. of crude p-isobutyl acetophenone (p-isobutylphenyl methyl ketone). The mixture is stirred and held at 17° to 19° C. while 7.60 g. of chloroacetonitrile in 18.0 ml. of toluene is added over 50 minutes. The reaction is followed by gas liquid chromatography analysis (GLC). If necessary, an additional 0.7 g. increment of chloroacetonitrile in 1.5 ml. portions of toluene is added over 10 minutes to complete the reaction. After stirring for an additional 1 hour to insure a complete reaction, 1 g. of a filter aid (Celite), 30 ml. of Skellysolve B and 50 ml. of water are stirred into the mixture. After filtration of the filter aid containing black residue the organic and aqueous phases are separated, the aqueous phase containing the sodium hydroxide is extracted with 35 ml. of Skellysolve B. The original organic phase and the Skellysolve B wash phase are washed with 30 ml. of water in sequence, combined, dried over sodium sulfate, and then concentrated to 24.71 g. of the 3-methyl-3-(p-isobutylphenyl)glycidonitrile as an oil of 93 percent purity by GLC analysis. The approximate yield by vapor phase chromatography methods in one run was over 95 percent.

This 3-methyl-3-(p-isobutylphenyl)glycidonitrile is useful as an intermediate to prepare ibuprofen, [2-(p-isobutylphenyl)propionic acid] a known antiinflammatory drug. For example, this glycidonitrile can be converted via the procedures described in Argentina Pat. Nos. 198,097, or 198,595 to make 2-(p-isobutylphenyl)propionic acid.

EXAMPLE 2

To a stirred reaction mixture containing 0.095 mole of p-isobutylacetophenone and 12.0 g. of flake sodium hydroxide in 12 ml. of N,N-dimethylformamide, there is added 0.10 mole of chloroacetonitrile over a 17 minute addition time at 14°-17° C. The mixture is allowed to stir for two hours to effect reaction. Then, an additional 0.02 mole of chloroacetonitrile is added over 5 minutes and the mixture is stirred for an additional 0.75 hour. Thereafter, 50 ml. of toluene and 50 ml. of water are added to the reaction mixture. Phases are separated. The aqueous phase is washed with 30 ml. of toluene. The toluene phase is washed with three 30 ml. portions of water to remove from the toluene phase as much of the dimethylformamide as is possible. The toluene phase containing the glycidonitrile is then concentrated to remove toluene and any residual water and to leave the 3-methyl-3-(p-isobutylphenyl)-glycidonitrile, 22.15 g. product as a neat liquid or in some portion of the toluene, say as a 25–30 percent glycidonitrile solution in toluene until it is ready for use.

Such solution form of the glycidonitrile can be used directly in processes for making ibuprofen, an anti-inflammatory carboxylic acid drug by the above referenced ionic Lewis acid process. The neat or substantially pure glycidonitrile is preferred when it is to be used to prepare the carboxylic acid via a halo-acylation procedure by reaction of the glycidonitrile with an acyl halide such as acetyl chloride to form the 2-acyloxy-3-halopropionitrile intermediate which is then dehydrohalogenated to form the 2-acyloxyacrylonitrile (enol acylate) intermediate. The enol acylate is treated aqueous alkali metal hydroxide to form the carboxylic acid salt and the carboxylic acid salt is treated with a strong acid to form the useful free carboxylic acid.

EXAMPLE 3

To a stirred mixture containing 0.095 mole of p-isobutylacetophenone and 0.293 molar equivalents of pelleted sodium hydroxide in 12 ml. of N,N-dimethylformamide there is added a mixture of 0.10 mole chloroacetonitrile and 18 ml. of toluene over a 17 minute period. The mixture is stirred and allowed to react for 2.1 hours. Then an additional 0.015 mole of chloroacetonitrile and 3 ml. of toluene are added over 5 minutes and the mixture is stirred for an additional 1 hour to insure complete reaction. To the reaction mixture there is added 50 ml. of toluene and 50 ml. of water. Phases are separated. The aqueous phase is washed with 40 ml. of toluene to extract any residual glycidonitrile therefrom. The toluene phases are washed with three 30 ml. portions of water to extract any dimethylformamide therein. The toluene phase is dried over sodium sulfate and concentrated to give 3-methyl-3-(p-isobutylphenyl)glycidonitrile (21.89 g.). Vapor phase chromatographic analysis of the glycidonitrile product showed it to contain over 95 percent yield of glycidonitrile, compared to a control standard of the same purified compound.

EXAMPLE 4

A mixture of 0.095 mole of p-isobutylacetophenone, 12.3 g. of flake sodium hydroxide and 0.10 mole of chloroacetonitrile in 18 ml. of toluene and only 0.5 ml. of N,N-dimethylformamide (DMF) was stirred for 2.1 hours. Analysis of samples by gas liquid chromatography indicated that no detectable reaction had occurred. An additional 0.5 ml. of DMF was added and the mixture was stirred for an additional 1 hour before taking a sample for analysis. Only a trace of product had been formed. Then a third 0.5 ml. portion of DMF was added and the mixture was stirred for an additional hour. Analysis showed the reaction was almost half complete. This procedure was repeated with a fourth 0.5 ml. portion of DMF. Analysis indicated reaction was still progessing but incomplete. When a fifth 0.5 ml. portion of DMF was added and stirred for 2.5 hours analysis showed increased product. Then to insure complete reaction of the ketone an additional 0.0132 mole of chloroacetonitrile was added together with an additional 0.5 ml. of DMF and 1.5 ml. of toluene. The mixture was stirred for an additional 0.5 hours to complete the reaction. Iced water (50ml.) and Skellysolve B (30 ml.) were added. The phases were separated. The aqueous phase was washed with Skellysolve B. (40 ml.). The organic extracts were washed in sequence twice with 30 ml. portions of water, dried over sodium sulfate and concentrated to 22.11 g. Assay indicated greater than 95 percent purity of 3-(p-isobutylphenyl)-3-methylglycidonitrile.

EXAMPLE 5

To a mixture of 0.095 ml. of p-isobutylacetophenone, 8.1 g. of technical grade, flake sodium hydroxide, in 4 ml. of DMF there was added 0.10 mole of chloroacetonitrile (diluted to 26.1 ml. with toluene) over 60 minutes. The mixture was stirred for 1.5 hours at about 15° C. The mixture was treated with an additional 10 percent of chloroacetonitrile, added over a 5 minute period and stirred for a total of 3.85 hours at 15° to 20° C. The reaction mixture was then treated with 40 ml. of Skellysolve B and 50 ml. of water. After phases separated the aqueous phase was removed and washed with 40 ml. of Skellysolve B. The organic phases were washed with two 30 ml. portions of water to remove the DMF. The organic phase containing the 3-methyl-3-(p-isobutylphenyl)glycidonitrile was treated with two portions of a filter aid to remove a minor amount of block residue from the solution. After drying and concentration the glycidonitrile product weighed 22.58 g. It was greater than 95 percent pure by gas liquid chromatography.

EXAMPLE 6

Following the procedure of Example 1 but substituting an equivalent amount of dimethylsulfoxide for the DMF there is obtained the 3-methyl-3-(p-isobutylphenyl)glycidonitrile.

EXAMPLE 7

Following the procedure of Example 1 but substituting an equivalent amount of dimethylacetamide (DMAC) for the DMF therein, there is obtained the 3-methyl-3-(p-isobutylphenyl)glycidonitrile.

EXAMPLE 8

Following the procedure of Example 1 but substituting an equivalent amount of hexa methyl-ortho-phosphoramide for the DMF therein, there is obtained the 3-methyl-3-(p-isobutylphenyl)glycidonitrile.

I claim:

1. A process for preparing a glycidonitrile of the formula

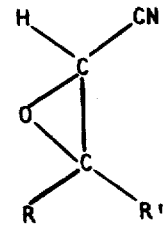

wherein R is aromatic and
R' is an aliphatic group,
which comprises reacting a ketone or aldehyde of the formula

where R and R' are as defined above with chloroacetonitrile in the presence of a solid form alkali metal or alkaline earth metal hydroxide in a solvent mixture containing at least about 3 percent by liquid volume of a dipolar aprotic, organic solvent under substantially anhydrous conditions.

2. Process according to claim 1 wherein the dipolar, aprotic organic solvent is selected from the group consisting of dimethylformamide, dimethylacetamide, dimethylsulfoxide, and hexamethyl-ortho-phorphoramide.

3. Process according to claim 1 wherein the reaction mixture contains a major proportion by volume of a nonpolar organic liquid solvent.

4. Process according to claim 3 coherein the nonpolar organic liquid is toluene.

5. Process of claim 1 wherein the reaction mixture contains at least about 6 percent by volume of the aprotic dipolar organic solvent.

6. Process according to claim 1 wherein p-isobutylacetophenone is reacted with chloroacetonitrile under substantially anhydrous conditions in the presence of solid form alkali metal hydroxide in a reaction mixture containing at least about 3 percent by volume, based on the volume of the total reaction mixture, of a dipolar, aprotic liquid solvent, any remaining solvent being a nonpolar, organic liquid, at from about 0° C. to about 50° C. to form 3-methyl-3-(p-isobutylphenyl)glycidonitrile.

7. Process according to claim 6 wherein the dipolar, aprotic liquid solvent is dimethylformamide.

8. Process according to claim 6 wherein toluene is used as a non-polar, organic solvent, in the reaction mixture.

* * * * *